United States Patent [19]

Mahurkar

[11] 4,443,333
[45] Apr. 17, 1984

[54] PORTABLE DIALYSIS SYSTEM AND PUMP THEREFOR

[76] Inventor: Sakharam D. Mahurkar, 1926 W. Harrison St., Chicago, Ill. 60612

[21] Appl. No.: 305,202

[22] Filed: Sep. 24, 1981

[51] Int. Cl.$^3$ ............................................. B01D 31/00
[52] U.S. Cl. ........................................ 210/87; 210/90; 210/96.2; 210/321.3; 210/416.1
[58] Field of Search ............... 417/475, 476, 477, 521, 417/531, 532; 210/85, 87, 90, 96.2, 321.3, 416.1

[56] References Cited

U.S. PATENT DOCUMENTS

| | | | |
|---|---|---|---|
| 4,083,777 | 4/1978 | Hutchisson | 210/96.2 X |
| 4,085,047 | 4/1978 | Thompson | 210/96.2 |
| 4,153,554 | 5/1979 | Heide et al. | 210/96.2 X |
| 4,181,610 | 1/1980 | Shintani et al. | 210/96.2 X |
| 4,190,536 | 2/1980 | Grimsrud | 210/416.1 X |
| 4,229,299 | 10/1980 | Savitz et al. | 210/96.2 X |
| 4,334,988 | 6/1982 | Milligan | 210/416.1 X |

*Primary Examiner*—Frank A. Spear, Jr.
*Attorney, Agent, or Firm*—Emrich & Lee and Brown, Hill, Dithmar, Stotland, Stratman & Levy

[57] ABSTRACT

A system for dialyzing blood in which blood is passed through an exchange station to transfer toxic material across a semipermeable membrane to a dialyzate. Pump means are disclosed for simultaneously pumping a plurality of liquids through the system at different flow rates. The pump means is provided with mechanism for stopping the flow of dialyzate while retaining the blood pumping capability.

10 Claims, 8 Drawing Figures

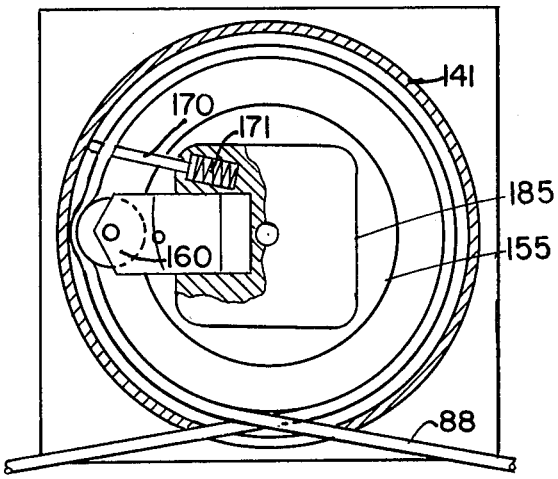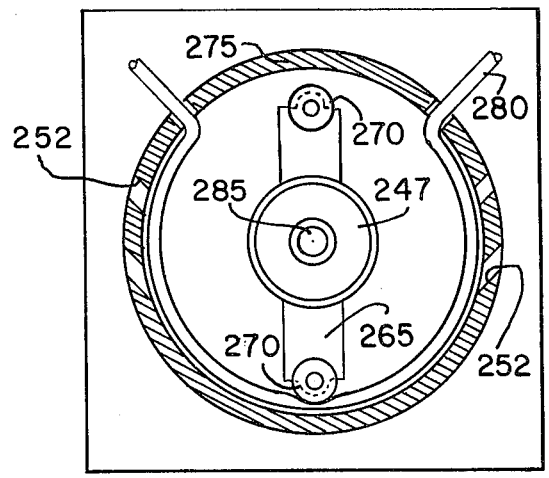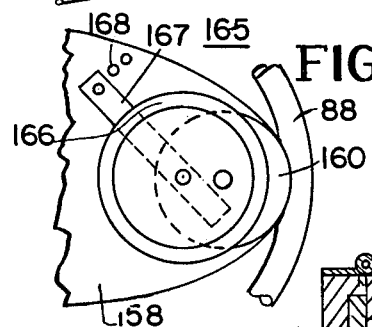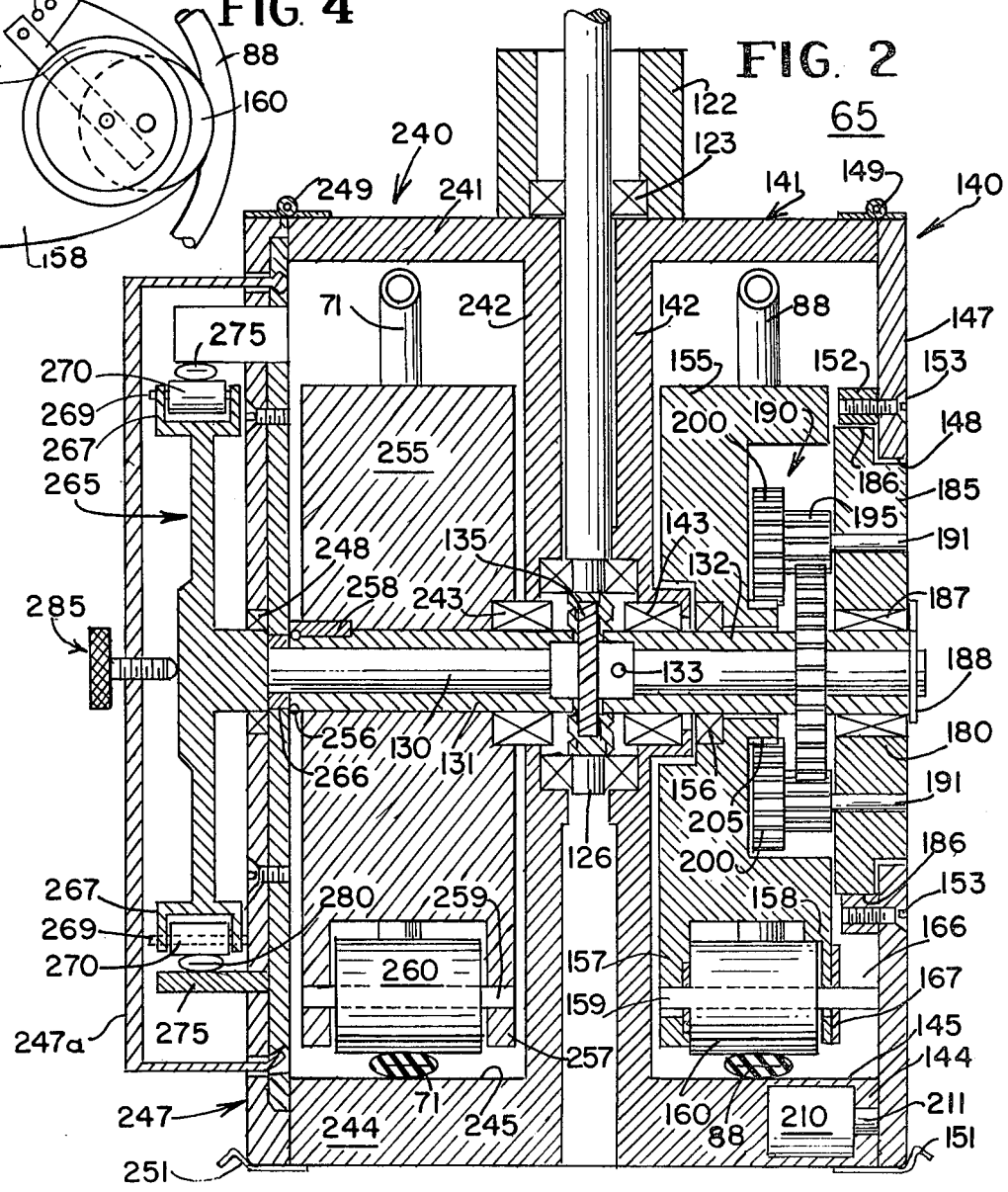

PORTABLE DIALYSIS SYSTEM AND PUMP THEREFOR

BACKGROUND OF THE INVENTION

Growing numbers of persons require dialysis due to acute or end stage renal disease. The majority of dialysis conducted in the United States involves the patient occupying a treatment facility for a period of up to about 6 hours as often as 2 or 3 times a week. Only a small fraction of people requiring diaylsis are able to dialyze themselves effectively at home. Still fewer people requiring dialysis are able to travel, since the attendant machinery is cumbersome.

Most prior art systems require several pumps in order to complete treatment. In general, there is required at least a blood pump, a dialysate pump and a pump for an anti clotting agent. The requirement of no less than two distinct pumps is a serious obstacle to providing a dialysis system sufficiently compact to enable free movement of the patient requiring the treatment. Another factor in the design of a dialysis system is the extraordinary cost of all the multiple components, and a significant factor in designing systems for developing countries is to reduce the cost of manufacture and maintenance to enable countries less affluent than the United States to provide the required number of systems to accommodate all persons requiring dialysis.

RELATED APPLICATION

This is an improvement of the invention disclosed in my prior U.S. patent application Ser. No. 822,229, filed Aug. 5, 1977 for PORTABLE DIALYSIS SYSTEM AND PUMP THEREFOR, now abandoned.

BRIEF SUMMARY OF THE INVENTION

It is a general object of the present invention to provide a compact, easy to manufacture dialysis system in which a single pump does the work of three.

Another object of the present invention is to provide a dialysis system utilizing a single pump for pumping multiple liquids at different flow rates.

A further object of the present invention is to provide a dialysis system in which a single pump is capable of pumping multiple liquids at different flow rates and is provided with mechanism for stopping the pumping of selected ones of the liquids without stopping the pumping of others of the liquids.

An important object of the present invention is to provide a fluid pumping device for use in a system for dialysing blood by passing blood and dialysate in mass transfer relation, the device comprising a single motor having the output shaft thereof connected to at least two peristaltic pumps one for transporting blood in an elastic blood tube and the other for transporting dialysate in an elastic dialysate tube, mechanism associated with the motor and the peristaltic pumps for maintaining the dialysate flow at about three times the blood flow, each of the peristaltic pumps having an inner arcuate bearing surface, the blood pump having at least one roller associated with the inner arcuate bearing surface to trap the blood tube therebetween, the dialysate pump having a single roller associated with the inner arcuate bearing surface to trap the dialysate tube therebetween, actuation of the peristaltic blood pump causing smooth laminar flow of blood in the blood tube due to the roller, actuation of the peristaltic dialysate pump causing flow due to a vacuum generated by the single roller resulting in the deformation and return of the elastic dialysate tube, and means for selectively stopping dialysate flow while maintaining blood flow or for simultaneously stopping all fluid flow.

A still further object of the present invention is to provide a lightweight and portable system for dialysing blood wherein blood passes through an exchange station with the blood contacting one side of a semipermeable membrane and dialysate contacting the other side of the semipermeable membrane, the system comprising elastic tube means adapted to be connected to a blood source and to return blood thereto for conducting blood past a plurality of stations, a blood clot detector and an air bubble detector in communication with said blood tube means, elastic tube means adapted to be connected to a source of dialysate for conducting dialysate past a plurality of stations, means for measuring and regulating dialysate flow, pressure, temperature and conductivity, means for maintaining the dialysate at a lower pressure than the blood during passage through the exchange station, a single motor means having the output shaft thereof connected to at least two peristaltic pumps one for transporting blood in the elastic blood means and the other for transporting dialysate in the elastic dialysate tube means, mechanism associated with the motor means and the peristaltic pumps for maintaining the dialysate flow at about three times the blood flow, each of the peristaltic pumps having an inner arcuate surface, the blood pump having at least one roller associated with the inner arcuate bearing surface to trap the blood tube means therebetween, the dialysate pump having a single roller associated with said inner arcuate bearing surface to trap said dialysate tube means therebetween, actuation of the peristaltic blood pump causing smooth laminar flow of blood in the blood tube means due to the roller, actuation of the peristaltic dialysate pump causing dialysate flow due to a vacuum generated by the single roller resulting in the deformation and return of the elastic dialysate tube means, and control mechanism operatively connected to the blood leak detector and the air bubble detector and to the motor means and to the dialysate flow, pressure, temperature and conductivity measuring means for selectively stopping the dialysate roller thereby halting movement of dialysate through the dialysate tube means and through the exchange station in response to pressure or temperature or conductivity measurements outside of a preselected range while maintaining blood flow and for simultaneously stopping all the rollers in response to a signal from either the blood leak detector or the air bubble detector to shut down the entire system and halt pumping.

These and other objects of the present invention will be more readily understood by reference to the following specification taken in conjunction with the accompanying drawings, in which:

BRIEF DESCRIPTION OF THE DRAWINGS

FIG. 2 is a view in section of the pump used to move the dialysate, blood and the anti clotting agent;

FIG. 4 is an end elevational view of the roller adjusting mechanism of the pump illustrated in FIG. 2;

FIG. 5 is a side elevational view of the roller assembly in pumping relationship with the dialysate tubing;

FIG. 6 is a side elevational view of the roller assembly in pumping relationship with anticoagulant delivery tubing;

FIG. 8 is a top plan view of an alternate pump for dialysate and blood flow.

DESCRIPTION OF THE PREFERRED EMBODIMENT

Figure 1:
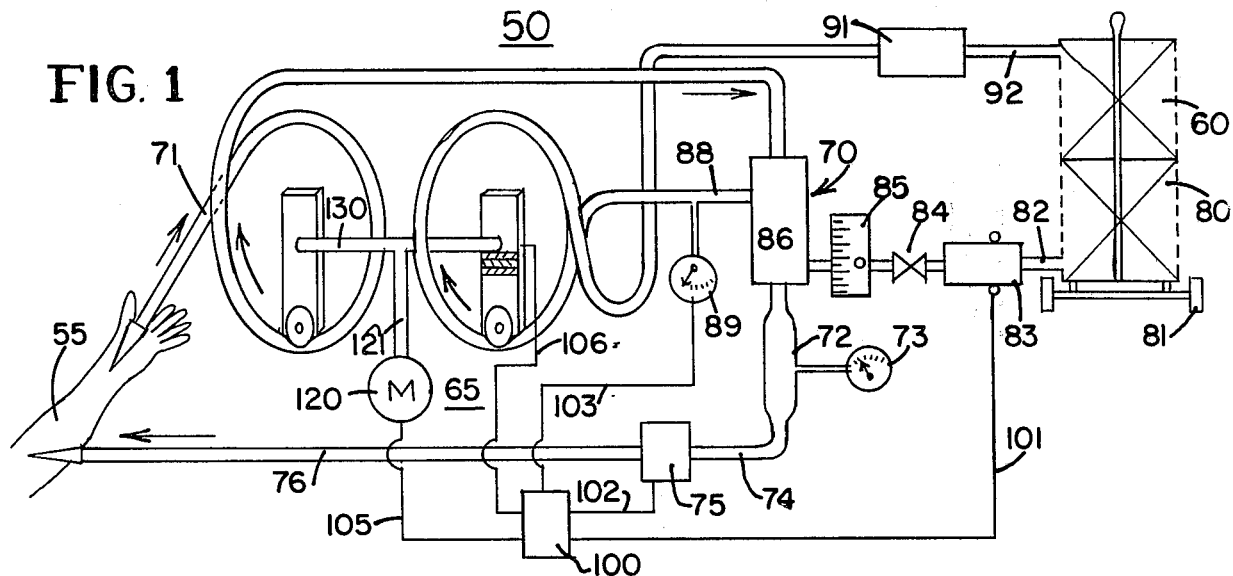
FIG. 1 is a schematic diagram of a dialysis system showing the blood source, the dialysate source and all mechanisms therebetween.

Referring now to FIG. 1, there is disclosed a dialysis system 50 in which there is provided a blood source 55 and a dialysate source 60. Intermediate the blood source 55 and the dialysate source 60 is a pumping station 64, which serves to pump blood from the blood source 55 and dialysate from the dialysate source 60 to an exchange station 70 wherein the blood and the dialysate are brought into contact across a semipermeable membrane, as is well known in the art, to effect transfer of various toxic materials from the blood to the dialysate. Specifically, a tube 71 leads from the source of blood 55 through the pumping station 65 to the exchange station 70. After blood passes through the exchange station 70, a pressure gauge 72 having a read-out device 73 measures the venus pressure in the tube 74. A bubble detector 75 is provided intermediate the exchange station 70 and the source of blood 55, and a tube 76 returns the blood as it flows from the bubble detector 75 to the source of blood 55.

The source of dialysate 60 is stored in a container 80 which is portable by means of wheels 81 and is collapsible. A dialysate exit 82 is positioned at the bottom of the container 80 and conducts dialysate from the container to a temperature and conductivity meter 83. Dialysate flowing through the meter 83 passes through a negative pressure valve 84 and into a flow meter 85. A tube 86 from the flow meter 85 conducts the dialysate to the exchange station 70 where flow between the dialysate and the blood is countercurrent. Dialysate exits the exchange station 70 at 88 through a dialysate drip chamber and accumulator 110, at which time a pressure meter 89 measures the dialysate pressure to ensure it is less than the blood pressure. The dialysate leaving the exchange station 70 passes via the tube 88 through the drip chamber and accumulator 110, the pumping station 65 and hence to a toxin remover 91 which may be activated charcoal and thence through the dialysate inlet 92 to the storage device 80.

Figure 7:
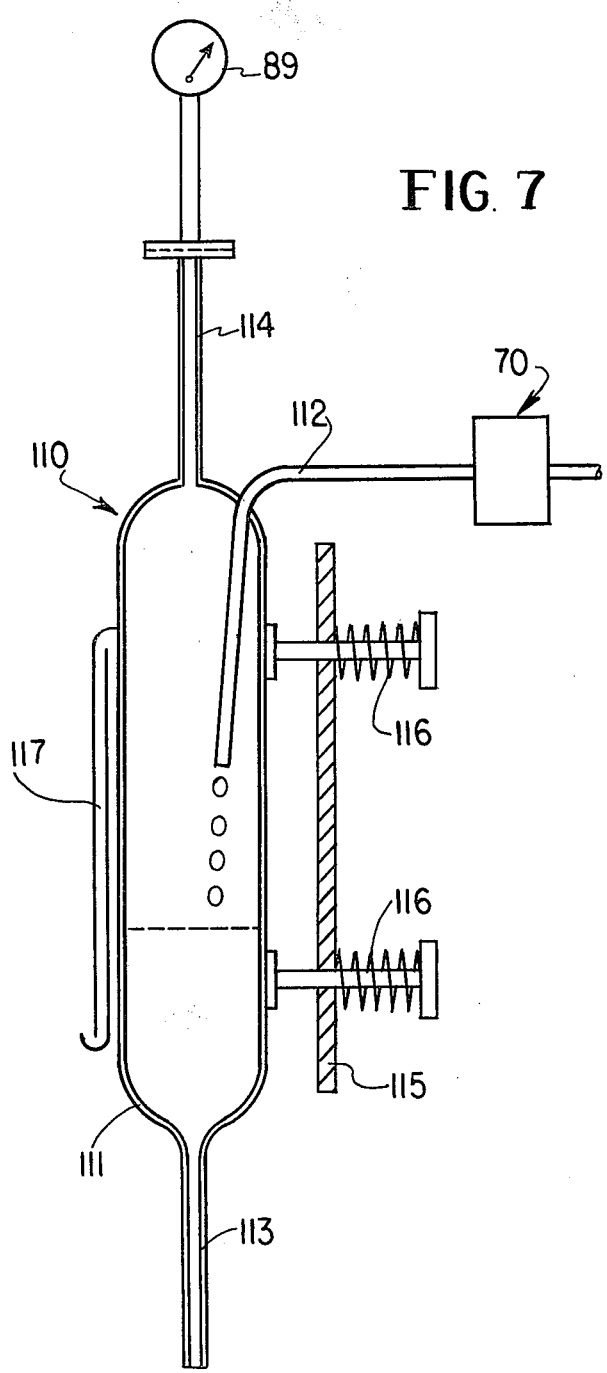
FIG. 7 is a side elevational view of a dialysis drip chamber.

The drip chamber and accumulator 110 (see FIG. 7), includes an elongated tubular body 111 of a synthetic organic resin which has an outlet tube 112 connected to the exchange station, thereby ensuring that the dialysate leaving the station 70 passes through the device 110. An exit 113 interconnects the body 111 with the pumping station 65. A tube 114 connects the pressure gauge 89 with body 111 to provide a reading of the dialysate pressure. The vacuum produced in the dialysate line by the pumping station 65 is controlled by varying the wall tension of the body 111 with the plates 115 and spring loaded adjusting screws 116. Finally, a hanger 117 permits the drip chamber 110 to be conveniently stored at the bed side.

Since the pumping station 65 moves liquid by successively compressing the liquid bearing tubes, suction in the tubing is created which in the absence of the drip chamber 110 could undesirably vary the dialysate flow rate and the ultrafiltration rate. The drip chamber 110 allows the maximum vacuum to be maintained constant in the dialysate side of the system which enhances the ultrafiltration. Specifically, increasing the wall tension of the body 111 by loosening the screws 116 will increase the vacuum in the system and decreasing the wall tension by tightening the screws will decrease the vacuum. When dialysate is present in the drip chamber 110, the coaction of the dialysate accumulation and the wall tension results in the vacuum being maintained within a given range and its magnitude being controlled.

A control mechanism 100 is provided and receives signals via lead 101 from the temperature and conductivity meter 83 and receives signals via lead 102 from the bubble detector 75 and receives a signal via the lead 103 from the dialysate pressure gauge 89. The control mechanism 100 is connected via lead 105 to a motor 120 in the pumping station 65 and via lead 106 to the dialysate pumping portion of the pumping station 65, as will hereinafter be explained.

Referring to FIG. 2, there is disclosed the pump portion of the pumping station 65, in which an output shaft 121 from the motor 120 in a shaft housing 122 is provided with bearing 123 for rotation with respect thereto. Toward the end of the drive shaft 121, there is provided a worm gear 125, see FIG. 3, and an end cap 126 at the distal end of the shaft 121. A pump shaft 130 is positioned perpendicularly to the motor drive shaft 121 and is provided with a pump shaft sleeve 131 (on the left-hand side) and a pump shaft sleeve 132 (on the right-hand side), the sleeves 131 and 132 being keyed to the shaft 130 as at 133. A pump drive gear 135 is mounted centrally of the shaft 130 and is keyed thereto as at 136 and is in geared relation with the worm gear 125, whereby rotation of the output shaft 121 of the motor 120 causes rotation of the pump shaft 130 and hence the sleeves 131 and 132 fixedly connected thereto.

Referring now to the right-hand portion of FIG. 2, there is provided a housing 140 comprised of a cylinder 141 having a circular rear wall 142 having bearings 143 centrally located therein to accommodate the pump shaft sleeve 132. An arcuate or circular end wall 144 extends perpendicularly outwardly from the rear wall 142 and has an inner surface 145. A cover 147 is connected to the end wall 144 by spaced apart hinges 149 and is provided with a square opening having rounded corners 148 therein. Spaced apart clips 151 are provided at the distal end of the cover 147 to ensure that the cover 147 normally remains closed.

The opening 148 is framed by a straight bar 152 mounted to the interior of the cover 147 a predetermined distance from the opening 148 by a plurality of screws 153. The bar 152 provides a friction surface for a purpose hereinafter set forth and may be any material suitable therefor.

A hub 155 is mounted for rotation about the sleeve 132 and is provided with bearings 156. The hub is circular in plan view and is provided with a finger 157 at one end thereof and a finger 158 spaced therefrom. A shaft 159 extends through the finger 157 and has a roller 160 mounted thereon. A roller adjustment mechanism 165 is associated with the finger 158 and the roller 160, as particularly seen in FIG. 4. The roller adjustment mechanism 165 includes a cam ring 166 and a cam lever 167, the cam lever having a plurality of adjustment positions 168 on the finger 158. The connection of the lever 167 and the finger 158 provides the required stability for the roller 160. The eccentric mounting of the cam ring 166 with respect to the roller 160, provides movement of the roller 160 toward and away from the associated inner surface 145 of the housing 140, in response to movement of the cam lever 167 among the various positions 168 thereof.

Also associated with the hub 155 is a tube guide rod 170, see FIG. 5, which precedes the roller 160 during rotation thereof, the rod 170 being spring loaded as at 171 to assure the associated dialysate tube 88 is in proper position to be trapped between the roller 160 and the associated arcuate support surface 145. The rod 171 can be pushed in while loading the tube 88.

Figure 3:
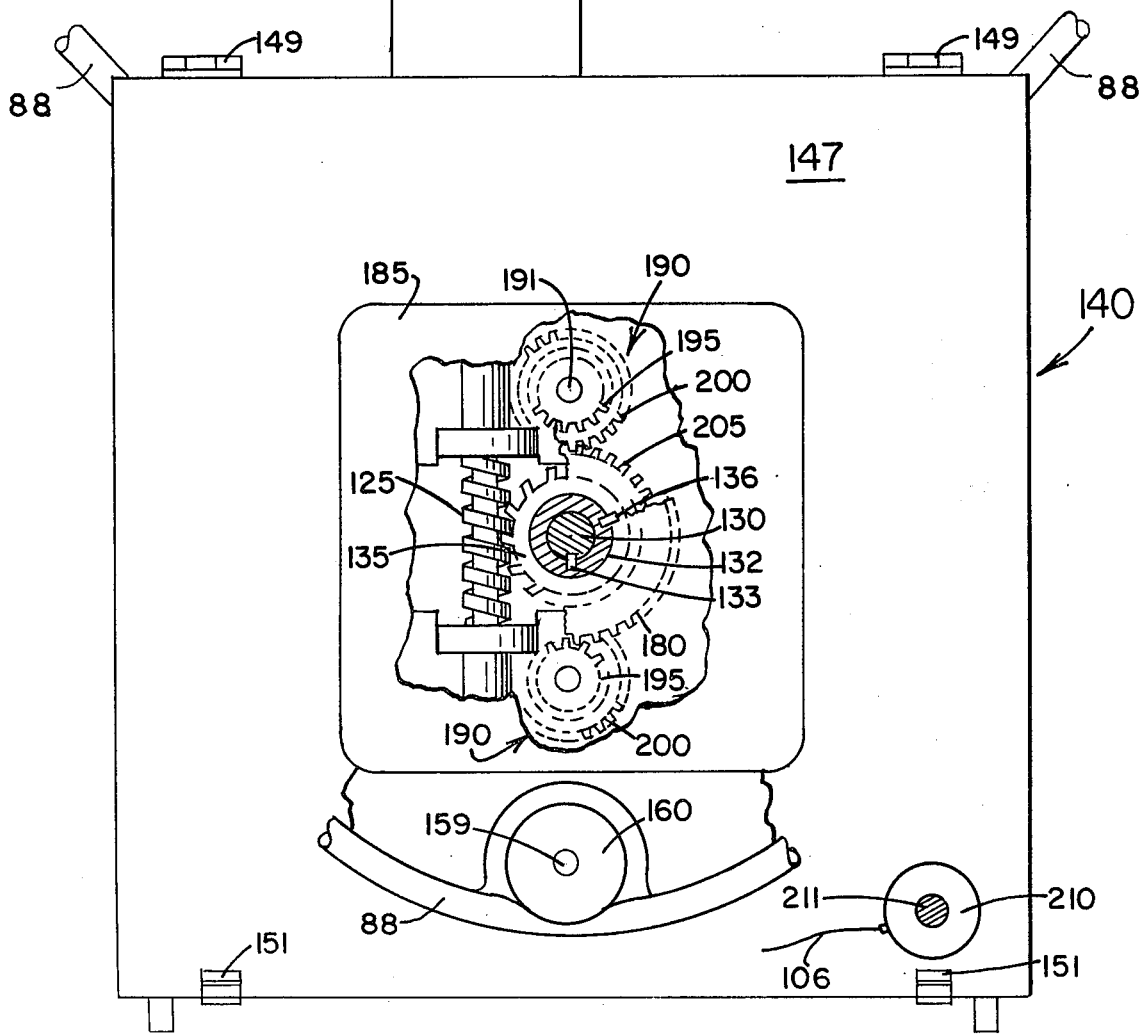
FIG. 3 is an end elevational view of the pump illustrated in FIG. 2 partially broken away to illustrate more specifically the gearing relationship of the dialysate side of the pump.

Referring now to the gearing arrangement particularly shown in FIGS. 2 and 3, there is a drive gear 180 fixedly mounted to the pump shaft sleeve 132 and maintained thereon by means of the key 136. An idler plate 185, square with rounded corners, is mounted for rotation about the pump shaft sleeve 132 and is provided with bearings 187. The distal edge 186 of the idler plate 185 is a friction surface and is positioned to be in frictional contact with the circular bar 152. The idler plate 185 is retained on the sleeve 132 by means of a snap ring 188.

Spaced apart idler gears 190 are provided in the idler plate 185 and specifically, each of the idler gears 190 is mounted on a shaft 191 frictionally retained in an appropriate aperture in the plate 185. Each idler gear 190 is provided with a small diameter gear 195 in driving relationship with the drive gear 180 and a larger diameter gear 200 in driving relationship with gear teeth 205 on the interior of the hub 155. Finally, a solenoid 210 connected to the control mechanism 100 by the lead 106 is mounted on the housing 140 near the distal end of the cover 147, and has a plunger 211, which upon activation of the solenoid, extends outwardly to open the cover 147, all for a purpose hereinafter set forth.

Referring now to the left-hand portion of the pumping station 65, there is disclosed a housing 240 in the form of a cylinder 241 having a circular rear wall 242 provided with central bearings 243 adapted to receive therethrough the pump shaft sleeve 131. The housing 240 includes an upstanding wall 244 extending perpendicular from the rear wall 242 and provided with an inner arcuate support surface 245.

A cover 247 extends over the circular opening of the cylinder 241 and is hingedly connected thereto as at spaced apart hinges 249. The cover 247 has a central bearing 248 surrounding an aperture therein and has an outer cover 247A mounted thereto. The outer cover 247A is circular in plan view and is cylindrical in shape, the cover 247A being adapted to snap fit within the cover 247. Spaced apart clips 251 are provided near the rim of the wall 244 and are adapted to retain the cover 247 in a closed position.

A hub 255 is mounted on the shaft sleeve 131 and is retained in place by a snap ring 256. The hub 255 is keyed to the sleeve 131 by means of an insert 258 and is provided with spaced apart parallel fingers 257 at one end thereof which accommodate a shaft 259 extending therebetween. A roller 260 is mounted on the shaft 259 and is free to rotate with respect to the hub 255.

An outer disc 265 is mounted to the shaft 130 by means of a mounting member 266 such that the disc 265, when mounted on the shaft, as well as the hub 255, rotate in response to rotation of the shaft 130. The disc 265 is provided with spaced apart mounting fingers 267 at both ends thereof, which fingers accommodate shafts 269 supporting rollers 270 thereon. An arcuate support surface 275 extends outwardly from the cover 247 and is adapted to trap a tube 280 between the arcuate support surface 275 and the rollers 270.

An adjustment knob 285 in the outer cover 247A serves to maintain the disc 265 in frictional engagement with the shaft 130 or may be adjusted to allow disengagement of the disc 265 from the shaft 130, as desired.

The wall of the cylinder 275, is provided with a plurality of apertures 252, as seen particularly in FIG. 6, to vary the length of the anticoagulant tubing 280 positioned on the inside of the cylinder. Specifically, by adjusting the tubing 280 into anyone of several of the slots 252 the length of tubing in contact with the inner surface of the cylinder 275 is controlled all for a purpose hereinafter set forth.

Rotation of the output shaft 121 of the motor 120, causes the pump shaft 130 to rotate through the coaction of the worm gear 125 and the gear 135. Since the hub 255 is fixedly mounted to the sleeve 131, which in turn is fixedly mounted to the shaft 130, rotation of the motor output shaft 121 causes rotation of the hub 255. As the housing wall 244 is circular, rotation of the hub 255 and hence the roller 260 carried thereby will cause liquid in the tube 71 trapped between the roller 260 and the adjacent side wall surface 245 to be propelled through the tube in a well known manner. It is this rotational action of the hub 255 carrying the roller 260 which causes liquid to be driven through the tubing 71 and causes the system 50 blood to travel from the source 55 thereof through the pumping station 65, the exchange station 70 and back to the source 55. Provided that the adjustment knob 285 is in position to cause frictional engagement between the disc 265 and the shaft 130, the disc 265 will rotate with the shaft 130 and the hub 255, thereby resulting in pumping of liquid in the tube 280 trapped between the arcuate support 275 and the roller 270, in the same manner previously described.

As seen from the foregoing, it is apparent that liquids in the tube 71 and 280, will be pumped so long as the motor 120 is activated and the shaft 121 is rotating. The dialysate side of the pumping station 65 operates in a different manner and is provided with mechanism for discontinuing pumping of the diaylsate in response to various conditions in the system 50 while the blood side of the pumping station remains active and pumping.

Specifically, although the drive gear 180 is fixedly mounted to the sleeve 132, which in turn is fixedly mounted to the shaft 130 and hence continuously rotates in response to rotation of the motor shaft 121, the hub 155 may or may not rotate depending on the position of the idler plate 185. As hereinafter before stated, there is gearing engagement between the idler plate 185 and the idler gears 190 mounted therein, which gearing engagement is sufficient to cause the idler plate 185 to rotate in response to rotation of the drive gear 180 in preference to the hub 155, provided the idler plate 185 is free to rotate and is not being restrained. That is, the idler gears 190 preferentially rotate the idler plate 185 rather than the hub 155 due to the difference in frictional engagement between the idler plate 185 and the shafts 191 mounted therein and the frictional engagement between the idler gears 200 and the bulb 205. When the door 147 of the housing 140 is open, the idler plate 185 is free to rotate above the sleeve 132, whereby rotation of the motor shaft 121 and hence the pump shaft 130 results in free rotation of the idler plate 185 and the hub 155 does not rotate. When the door 147 is closed, the frictional engagement between the bar 152 and the surface 186 of the idler plate 185 as well as with the door itself, is sufficient to prevent rotation of the idler plate 185. When the idler plate 185 is fixed against rotation, the idler gears 190 and specifically the engagement between the gears 200 and 205, cause the hub 155 to rotate, and hence, cause pumping of liquid in the tube 88 trapped between the roller 160 and the adjacent arcuate surface 145.

The gear ratio between the gears 180, the gears 190 and 205 is sufficient to cause a pumping ratio of dialysate blood to be between 2 and 3 to 1. That is, 2 to 3 times as much dialysate is pumped as is blood. The pumping ratio between dialysate and blood can be varied in several ways. By adjusting the gears hereinbefore mentioned, the hub 155 can be made to rotate faster than the hub 255. Another method of controlling the pumping ratio is to change the length of tubing in contact with the associated roller. As previously illustrated, with the anticoagulant pump 265, the length of tubing 71 carrying the blood therein in contact with the roller 260 can be varied to control the flow rate of blood. Another factor affecting flow rate is the amount of tube compression designed into the system for each sweep or rotation of the roller. Adjustment of the amount of tube compression is made by the adjusting mechanism 165 previously described.

An important feature of the present invention is the mechanism whereby activation of the solenoid 210 in response to a reading from the temperature and conductivity meter 83 or the pressure meter 89 results in the cover 147 being sprung open, thereby discontinuing rotation of the hub 155 and stopping pumping of the dialysate through the system 50. This is critical, since close control of dialysate temperature, concentration and pressure is necessary to insure the safety of a patient during dialysis. Additionally, the control mechanism 100 receives an input signal from the air bubble detector 75 and a standard blood leak detector normally located on the dialysate side past the exchange station 70 (not shown) and will disengage or deactivate the motor 120 in response to a signal from those sources, thereby ensuring that the hub 255 is stopped and blood is no longer pumped from the patient. As seen by the foregoing description, an anticoagulant such as Heprin in the tube 280 will automatically be pumped during pumping of the blood, and this is an added safety feature for the system 50.

From the foregoing, it will be seen that various numbers of liquids can be pumped individually or simultaneously and at varying flow rates. The pumping station 65 of the present invention is entirely capable of pumping multiple liquids each at a different flow rate. Further, it is clear from the foregoing description, that various safety mechanism can be built into the system to enable selective ones of various liquids to be pumped or not to be pumped in response to various parameters, three such liquids being illustrated in the foregoing description. Another feature of the present invention is the provision of a closed loop system, which enables dialysate to be taken from the source 60 thereof transported through the various metering devices and the exchange station 70 and then returned to the source thereof, thereby forming a closed loop. The pumping station 65 simultaneously is adaptable to pump both blood and an anticoagulant. This combination of three individual pumping capabilities housed in one small and relatively inexpensive to manufacture mechanism greatly facilitates the aforementioned principal object of the present invention, which is to provide a compact and inexpensive dialysis system.

Another feature of the present invention is that dialysate flow can be stopped by opening the door 147 without affecting blood pumping to allow adjustments to be made on the system 50 without disconnecting the blood tubing 71 from the patient. Anticoagulant flow rate can be adjusted or stopped without affecting blood pumping or dialysate pumping, a feature providing great flexibility to the system 50. The provision of the drip chamber 110 permits the maximum vacuum to be maintained on the dialysate side ensuring preferred ultrafiltration while maintaining the vacuum relatively constant due to the accumulation of dialysate in the chamber body 111.

Referring now to FIG. 8 of the drawings, there is disclosed an improved embodiment 300 for the pumping station 65. In the embodiment 300 there is provided a housing 305 for the drive mechanism, blood pump, and dialysate pump as will be explained, the blood pump having an end plate 306 pivotally connected to the housing 305 by means of the hinge 307, and similarly, the dialysate pump is provided with an end plate 308 pivotally connected to the housing 305 by means of a hinge 309. A motor (not shown) has an output shaft 310 thereof connecting to a worm gear wheel 312 via a gear 311 connected via a traditional sleeve member to the output shaft 310. A shaft 313 exits from the worm wheel 312, to the right as seen in the drawing, and is supported for rotation by bearings 314. A hub 316 is mounted on the shaft 313 and is connected for rotation with the shaft 313 by means of a clutch assembly 315.

The hub 316 is provided with a roller 317 journaled for rotation in the clevis portion of the hub 316. The roller 317 in combination with the hub 316 is dimensioned to compress the dialysate containing tube 318 which is positioned between the roller 317 and the adjacent portion of the housing 305, thereby to allow the dialysate tube 318 to be compressed as the roller 317 rotates. The clutch 315 positively engages the hub 316 and when the shaft 313 rotates in response to actuation of the output shaft 310 of the motor, the dialysate tube 318 is intermittently compressed to cause the dialysate to be pumped therein. In the event of an abnormality in the dialysate pressure, temperature or conductivity, a signal is transmitted to the clutch mechanism 315 which disengages the hub 316 from the shaft 313, thereby to allow the shaft to rotate but not the hub and hence the roller 317 connected thereto. This safety mechanism allows the dialysate pumping to stop while the blood pumping continues, as explained.

The output shaft 310 of the motor is connected via the worm gear 311 and roller 312 to a pair of circular pinion gears 321 and 322, the gear 322 has a diameter three times the diameter of gear 321, thereby to reduce the rotation of the shaft 323 connected thereby by a ratio of 3 to 1 compared to the rotation of the shaft 313. The shaft 323 is supported in bearings 324 similarly to the bearings 314, both shafts 313 and 314 being retained by the usual snap rings or other like mechanism. A hub 326 is mounted on a shaft 323 and is provided with two rollers 327, each mounted on a shaft in a clevis portion of the hub 326. The size of the hub 326 and the rollers 327 is such to compress a blood tube 328 between the rollers 327 and the adjacent portions of the housing 305. The multiple rollers 327 in the blood pump provides smooth, slow and steady blood flow through the pumping station while the single roller 317 on a dialysate side provides for intermittent pumping of dialysate through the pumping station which increases the vacuum on the diaylsate side and improves the ultrafiltration of the system.

For instance, if the shaft 313 rotates at about 90 rpm, then the shaft 323 rotates at about 30 rpm, thereby to provide the required slow and steady blood flow. As before stated, the preferred pumping ratio of dialysate to blood is between about 2 and about 3 to 1, so that if the shaft 313 rotates at 90 rpm the shaft 323 should rotate between 30 rpm and 45 rpm. Accordingly, if shaft 323 rotates at about 30 rpm, then shaft 13 should rotate between about 60 rpm and about 90 rpm; if shaft 323 rotates at about 45 rpm, then shaft 313 should rotate between about 90 rpm and about 135 rpm.

In the event of a rupture of the artificial kidney mechanism a blood leak detector or in the event of an electrical failure which causes the motor to stop and hence the output shaft 310 thereof to cease rotating, the entire system shuts down but the blood in the system can be returned to the patient by manual cranking of the blood side by inserting an appropriate tool in the slot 329 at the distal end of the shaft 323.

The embodiment 300 is an improvement over prior art devices since a single motor with the output shaft thereof provides for rapid rotation of the dialysate mechanism as compared to the blood mechanism thereby resulting in a dialysate pumping flow rate of about three times the blood flow rate. By using a single roller on the dialysate side, the vacuum in the dialysate side can be regulated by adjusting the volume of dialysate in the system with a lower volume causing a larger vacuum and thereby increasing the transmembrane pressure producing greater ultrafiltration. The intermittent pumping of the dialysate is therefore an improvement, while the continuous, slow and steady blood pumping is maintained as required for good blood treatment. The multiple rollers 327 on the blood side in combination with the single roller 317 on the dialysate side is a distinct improvement.

While there has been described what at present is considered to be the preferred embodiments of the present invention, it will be understood that various modifications and alterations can be made therein without departing from the true spirit and scope of the present invention and it is intended to cover in the appended claims all such modifications and variations.

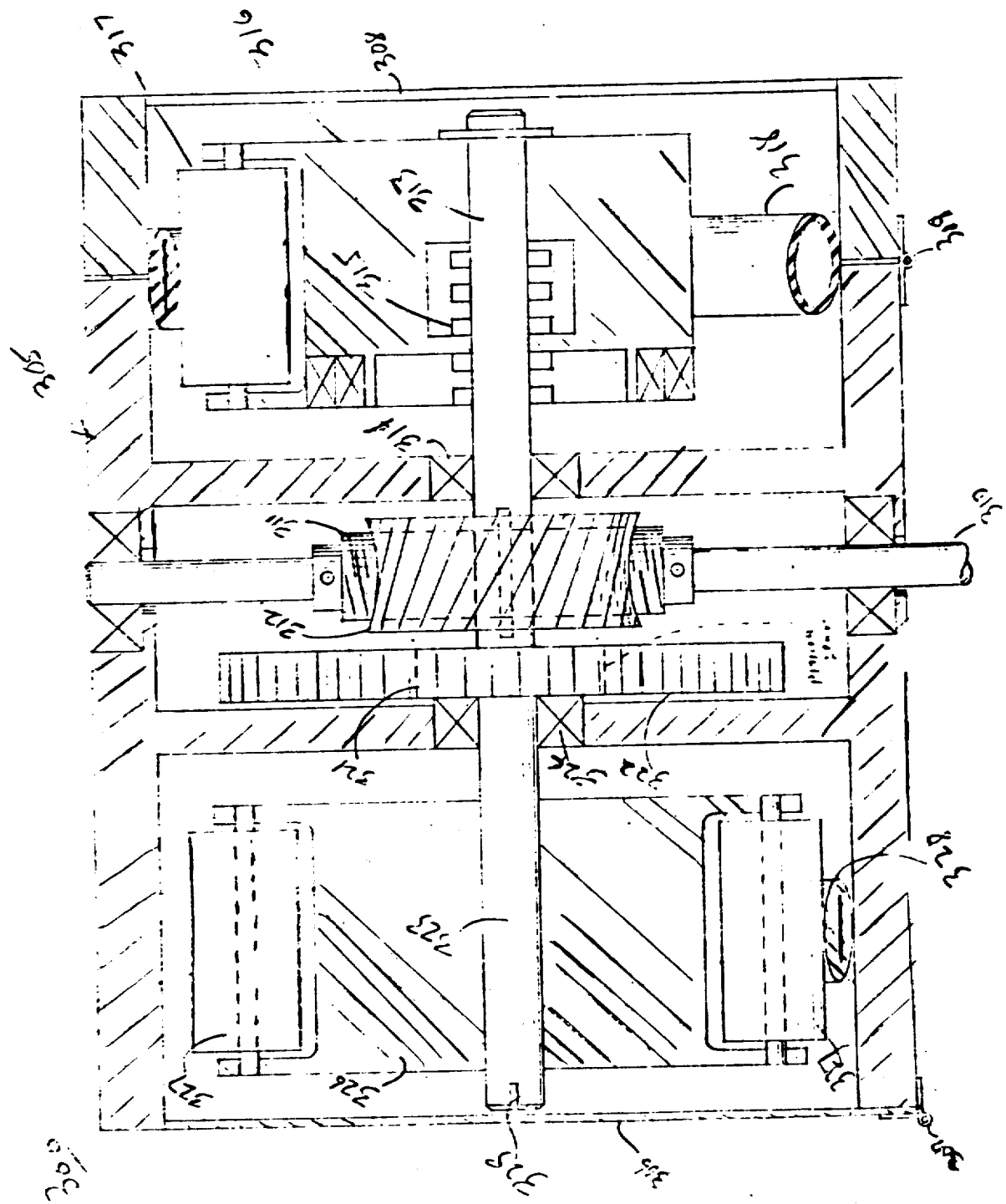

What is claimed is:

1. A fluid pumping device for use in a system for dialysing blood by passing blood and dialysate in mass transfer relation, said device comprising a single motor having the output shaft thereof connected to at least two peristaltic pumps one for transporting blood in an elastic blood tube and the other for transporting dialysate in an elastic dialysate tube, mechanism associated with said motor and said peristaltic pumps for maintaining the ratio of dialysate flow to blood flow in the range of from about 2 to about 3, each of said peristaltic pumps having an inner arcuate bearing surface, said blood pump having two rollers associated with said inner arcuate bearing surface to trap said blood tube therebetween, said dialysate pump having a single roller associated with said inner arcuate bearing surface to trap said dialysate tube therebetween, actuation of said peristaltic blood pump causing smooth laminar flow of blood in said blood tube due to said multiple rollers, actuation of said peristaltic dialysate pump causing dialysate flow due to a vacuum generated by said single roller resulting in the deformation and return of said elastic dialysate tube, and means for selectively stopping dialysate flow while maintaining blood flow or for simultaneously stopping all fluid flow.

2. The device of claim 1, wherein a third peristaltic pump for transporting an anti-clotting agent in an elastic tube therefor is selectively connected to said peristaltic blood pump to rotate therewith to pump an anti-clotting agent when blood is pumped or upon disengagement from said blood pump to permit independent movement of said blood pump.

3. The device of claim 1, wherein said means for selectively stopping dialysate flow while maintaining blood flow includes a drive gear fixedly mounted on said output shaft, an idler plate mounted for free rotation about said output shaft, an idler gear frictionally mounted on said idler plate in geared relation to said drive gear and in geared relation to a hub gear operatively connected to said dialysate pump roller, and means for fixing said idler plate against rotation, whereby when said idler plate is fixed against rotation said idler gear driven by said drive gear drives said hub gear and said dialysate pump roller and when said idler plate is free to rotate said idler gear driven by said drive gear drives said idler plate only without driving said hub gear and said dialysate pump roller.

4. The device of claim 1, wherein said mechanism for maintaining the ratio of dialysate flow to blood flow includes gear reduction means for causing the peristaltic blood pump rollers to rotate at about one third the speed of said peristaltic dialysate pump roller.

5. The device of claim 1, wherein said peristaltic blood pump rotates at about 30 rpm and said peristaltic dialysate pump rotates at about 90 rpm.

6. A lightweight and portable system for dialysing blood wherein blood passes through an exchange station with the blood contacting one side of a semipermeable membrane and dialysate contacting the other side of the semipermeable membrane, said system comprising elastic tube means adapted to be connected to a blood source and to return blood thereto for conducting blood past a plurality of stations, a blood clot detector and an air bubble detector in communication with said blood tube means, elastic tube means adapted to be connected to a source of dialysate for conducting dialysate past a plurality of stations, means for measuring and regulating dialysate flow, pressure, temperature and conductivity, means for maintaining the dialysate at a lower pressure than the blood during passage through the exchange station, a single motor means having the output shaft thereof connected to at least two peristaltic pumps one for transporting blood in said elastic blood tube means and the other for transporting dialysate in said elastic dialysate tube means, mechanism associated with said motor means and said peristaltic pumps for maintaining the dialysate flow at about three times the blood flow, each of said peristaltic pumps having an inner arcuate bearing surface, said blood pump having at least two rollers associated with said inner arcuate bearing surface to trap said blood tube means therebetween, said dialysate pump having a single roller associated with said inner arcuate bearing surface to trap said dialysate tube means therebetween, actuation of said peristaltic blood pump causing smooth laminar flow of blood in said blood tube means due to said rollers, actuation of said peristaltic dialysate pump causing dialysate flow due to a vacuum generated by said single roller resulting in the deformation and return of said elastic dialysate tube means, and control mechanism operatively connected to the blood clot detector and the air bubble detector and to said motor means and to the dialysate flow, pressure, temperature and conductivity measuring means for selectively stopping the dialysate roller thereby halting movement of dialysate through the dialysate tube means and through the exchange station in response to pressure or temperature or conductivity measurements outside of a preselected range while maintaining blood flow and for simultaneously stopping all the rollers in response to a signal from either the blood leak detector or the air bubble detector to shut down the entire system and halt pumping.

7. The system set forth in claim 6, wherein the motor means is adapted to move an anti-clotting agent from the source thereof to the blood at a predetermined flow rate.

8. The system set forth in claim 6, wherein said means for measuring and regulating dialysate pressure, temperature and conductivity includes a drip chamber and accumulator between the exchange station and the motor means having flexible walls and mechanism for varying the wall tension thereof to control the vacuum on the dialysate side of the system.

9. The system set forth in claim 6, wherein each peristaltic pump includes mechanism for varying the length of the tube means trapped between said bearing surface and the associated roller or rollers to vary the flow rate in the associated tube means.

10. The system of claim 6, wherein a third peristaltic pump for transporting an anti-clotting agent in an elastic tube therefor is selectively connected to said peristaltic blood pump to rotate therewith to pump an anti-clotting agent when blood is pumped or upon disengagement from said blood pump to permit independent movement of said blood pump.

* * * * *

UNITED STATES PATENT AND TRADEMARK OFFICE
CERTIFICATE OF CORRECTION

PATENT NO. : 4,443,333
DATED : April 17, 1984
INVENTOR(S) : Sakharam D. Mahurkar It is certified that error appears in the above-identified patent and that said Letters Patent are hereby corrected as shown below:

Figure 8 should be added as shown on the per attached sheet.

Signed and Sealed this

Sixteenth Day of April 1985

[SEAL]

Attest:

DONALD J. QUIGG

Attesting Officer

Acting Commissioner of Patents and Trademarks